United States Patent
Fenster et al.

(10) Patent No.: US 6,610,013 B1
(45) Date of Patent: Aug. 26, 2003

(54) 3D ULTRASOUND-GUIDED INTRAOPERATIVE PROSTATE BRACHYTHERAPY

(75) Inventors: Aaron Fenster, London (CA); Donal B. Downey, London (CA)

(73) Assignee: Life Imaging Systems, Inc., Ontario (CA)

(*) Notice: Subject to any disclaimer, the term of this patent is extended or adjusted under 35 U.S.C. 154(b) by 0 days.

(21) Appl. No.: 09/411,546

(22) Filed: Oct. 1, 1999

(51) Int. Cl.[7] ................................................ A61B 8/00
(52) U.S. Cl. ...................................................... 600/439
(58) Field of Search ................................ 600/437–439, 600/443, 7, 1, 3, 427; 601/2, 3, 4; 128/920, 924

(56) References Cited

U.S. PATENT DOCUMENTS

| | | |
|---|---|---|
| 5,205,289 A | 4/1993 | Hardy et al. |
| 6,027,446 A * | 2/2000 | Pathak et al. ............... 600/439 |
| 6,050,943 A * | 4/2000 | Slayton et al. .............. 600/439 |
| 6,095,975 A * | 8/2000 | Silvern ........................ 600/439 |
| 6,129,670 A * | 10/2000 | Burdette et al. ............. 600/427 |
| 6,200,255 B1 * | 3/2001 | Yu .................................. 600/1 |

FOREIGN PATENT DOCUMENTS

| | | |
|---|---|---|
| WO | WO 98/23213 | 6/1998 |
| WO | WO 98/23214 | 6/1998 |
| WO | WO 99/26534 | 6/1999 |

OTHER PUBLICATIONS

Tong et al., A Three–Dimensional Ultrasound Prostate Imaging System, *Ultrasound in Medicine & Biology*, vol. 22, No. 6, pp. 735–746 (1996).

* cited by examiner

Primary Examiner—Marvin M. Lateef
Assistant Examiner—Ali M. Imam
(74) Attorney, Agent, or Firm—Fulwider Patton Lee & Utecht, LLP (57) ABSTRACT

The present invention is directed to a 3D ultrasound-guided intraoperative brachytherapy method for the diagnosis and treatment of prostate cancer in men. The method comprises the steps of a pre-implant planning phase using 3D TRUS and semi-automated contouring, an implantation phase and a post plan verification phase for monitoring.

6 Claims, 13 Drawing Sheets

# 3D ULTRASOUND-GUIDED INTRAOPERATIVE PROSTATE BRACHYTHERAPY

FIELD OF THE INVENTION

The present invention is directed to the diagnosis and therapy of prostate cancer in men. More particularly, the invention is directed to a 3D ultrasound-guided intraoperative brachytherapy method for the diagnosis and treatment of prostate cancer.

BACKGROUND OF THE INVENTION

Prostate cancer is the most commonly diagnosed malignancy in men over the age of 50, and is found at autopsy in 30% of men at the age of 50, 40% at age 60, and almost 90% at age 90. Worldwide, it is the second leading cause of death due to cancer in men, accounting for between 2.1% and 15.2% of all cancer deaths. In Canada, about 20,000 new prostate cancer cases will be diagnosed and about 4,000 men will die from this disease every year.

Symptoms due to carcinoma of the prostate are generally absent until extensive local growth or metastases develop, accounting for the fact that only 65% of patients are diagnosed with locally confined disease. Once the tumour has extended beyond the prostate, the risk of metastasis increases dramatically. Tumours smaller than 1 to 1.5 cm$^3$ rarely broach the prostatic capsule. When diagnosed at this early stage, the disease is curable, and even at later stages treatment can be effective. Nevertheless, treatment options vary depending on the extent of the cancer, and prognosis worsens when diagnosis occurs at an advanced stage.

The prostate-specific antigen (PSA) blood test has become well established for early detection of prostate cancer, and for monitoring of prostate cancer particularly after treatment. The wide availability of the PSA test, the public's increased awareness about prostate cancer, and the growing number of men approaching the age of 50, have all combined to increase the proportion of prostate cancer diagnosed at an early-stage. Currently, 77% of men are diagnosed to have early stage prostate cancer, compared to only 57% between 1975 and 1979. Managing and treating these increasingly early stage cancers has generated a great deal of debate in both the medical community and the public.

The standard treatment regimens for prostate cancer are: watchful waiting, radical prostatectomy, external beam radiation, and brachytherapy. While watchful waiting is appropriate for some, the majority of men diagnosed with early stage cancer will request or need treatment. There is a growing belief that aggressive therapy may not be justified for early stage disease due to the morbidity (incontinence and impotence) of radical prostatectomy. External beam radiation is effective, but requires long treatment times and results in irradiation of normal tissues. Conformal radiation therapy of the prostate may reduce this problem, however, early reports are mixed. In addition, costs are high in treating and managing patients undergoing these traditional forms of therapy.

The challenges facing physicians managing patients with possible prostate cancer are to: (a) diagnose clinically relevant cancers at a stage when they are curable, (b) stage and grade the disease accurately, (c) apply the appropriate therapy accurately to optimize destruction of cancer cells while preserving adjacent normal tissues, (d) follow patients to assess side effects and the effectiveness of the therapy.

U.S. Pat. Nos. 5,562,095, 5,454,371 and 5,842,473 are directed to methods and systems for developing 3D ultrasound images which can be used for diagnosing clinically relevant cancers at curable stages and staging and grading the cancers. Hence these patents provide 3D ultrasound methods which address (a) and (b) as described above In the past 10 years improvements in imaging technology, computer aided dosimetry, and new treatment options have stimulated investigators to search for alternative approaches such as minimally invasive therapies for localized prostate cancer, e.g., brachytherapy, cryosurgery, hyperthermia, interstitial laser photocoagulation (ILP), and photodynamic therapy (PDT). Of these techniques, brachytherapy is the most advanced and is now considered to be a definitive treatment option for early stage prostate cancer.

Minimally-invasive procedures are revolutionizing surgery and therapy, because they offer significant reductions in patient morbidity, recovery time, hospital stay, and overall cost, while preserving or increasing clinical efficacy greatly benefiting both the patient and the health-care system. Clearly, a minimally invasive procedure for prostate cancer providing these benefits is welcome, especially because of the significant morbidity currently associated with traditional therapies. Because imaging is critically important to the safe delivery of the therapy, the major imaging companies are manufacturing CT (computer tomography) and MRI (magnetic resonance imaging) scanners that allow minimally invasive procedures to be performed under direct imaging guidance. However, conventional CT does not have real-time imaging capability, and both CT and MRI are expensive technologies requiring a special facility. Ultrasound is a much cheaper and more flexible imaging modality. Unlike CT or MRI, which are often located in dedicated suites specifically built to accommodate their needs, the ultrasound machine can be moved to the operating room as needed. Moreover, with ultrasound, the surgeon or therapist sees what is happening as it occurs, in real time. As a result, percutaneous ultrasound-guided prostate therapy techniques are currently under intense investigation.

It was therefore required, to provide a safe and effective minimally-invasive method for the diagnosis and therapy of prostate cancer that would not only allow for the application of appropriate therapy but also allow the assessment of patient side effects and the effectiveness of the therapy. The method of the present invention addresses these clinical requirements utilizing the benefits of 3D ultrasound together with intraoperative brachytherapy in order to provide a superior and more accurate method of assessing, suitably treating and following-up the progression and treatment of prostate cancer than currently known traditional methods.

SUMMARY OF THE INVENTION

In the present invention, the Applicant provides a novel method and system to apply an appropriate therapy accurately to the prostate and to follow-up with patients to assess side effects and the effectiveness of the therapy using 3D ultrasound imaging. Preferably, intraoperative brachytherapy of the prostate is done using TRUS. The present invention is an extension of the Applicant's developments in 3D ultrasound to 3D ultrasound-guided intraoperative brachytherapy.

The present invention utilizes a 3D ultrasound imaging system allowing all aspects of the procedure to be carried out intra-operatively, accurately and consistently in one session, including: semi-automated prostate margin and volume definition, real-time 3D implant guidance, verification of needle placement, and post-implant radioactive seed deposition verification. Dose planning is integrated with the present invention to allow near real-time (eg., 0.5 sec per seed) dose updates and on-line corrections of the plan based on the actual prostate implant geometry during the implantation.

In accordance with an object of the present invention there is provided a 3D ultrasound guided intraoperative method for the diagnosis and treatment of diseased tissues, the method comprising the steps of:

a pre-implant planning phase for producing a 3D tissue image comprising shape and volume of said tissue and surrounding structures and determining optimal distribution of a selected therapy;

a needle implantation phase for needle and positioning segmentation for delivery of the selected therapy to said tissue; and a post-plan monitoring phase to verify the therapy implantation and for allowing error correction.

Preferably, the method is used to diagnose and treat prostate cancer in men however, the method can be extended to diagnose and treat several different tissues such as the liver, breast and brain.

While the method is especially beneficial to treat prostate cancer with brachytherapy, the method may also be used with other therapies such as cryosurgery, photodynamic therapy, photocoagulation and thermal therapy.

In accordance with another object of the present invention there is provided a 3D ultrasound-guided intraoperative brachytherapy method for the diagnosis and treatment of prostate cancer, said method comprising: a pre-implant planning phase for producing a 3D image of the prostate and surrounding structures and determining optimal distribution of the brachytherapy; a needle implantation phase for needle segmentation and positioning for delivery of the brachytherapy to the prostate; and a post-plan monitoring phase for verifying the needle implantation of the brachytherapy and for allowing error correction during the needle implantation phase.

In accordance with a further object of the present invention there is provided a 3D ultrasound guided intraoperative system for the diagnosis and treatment of prostate cancer, said system comprising: a 3D TRUS transducer for producing a 3D image of said prostate and surrounding structures; a first computer means for determining a needle trajectory for optimal distribution of brachytherapy; at least one needle for implanting brachytherapy to said prostate along said needle trajectory; and a second computer means for verifying implantation of said brachytherapy to said prostate.

BRIEF DESCRIPTION OF THE DRAWINGS

A detailed description of the preferred embodiments is provided herein below with reference to the following drawings in which:

FIGS. 7A–7F show examples of three 3D TRUS examinations of patients with prostate cancer. FIGS. 7A and 7B are of a patient with a left base tumor (green arrows). The 3D images have been sliced in different planes to reveal the tumor. The coronal view cannot be obtained using conventional 2D TRUS. FIGS. 7C and 7D are of a patient with a subtle apical tumor [T and arrow, respectively). FIG. 7E shows contrast enhanced 3D TRUS image, showing increased vascularly on one side of the prostate. FIG. 7F shows the same 3D image as in 7E, but after maximum intensity projection from the coronal perspective showing the increased vascularly.

FIGS. 8A–8D show operating room 3D images of a 57 year old patient with recurrent prostate cancer following radiation three years previously.

Coronal "cut" which can only be obtain,ed with 3D TRUS shows (A) right needle has been deflected; and (B) correct insertion of needle after withdrawal and re-insertion

In the drawings, preferred embodiments of the invention are illustrated by way of example. It is to be expressly understood that the description and drawings are only for the purpose of illustration and as an aid to understanding and are not intended as a definition of the limits of the invention.

DETAILED DESCRIPTION OF THE PREFERRED EMBODIMENTS

The present invention is a novel method based on the use of 3D ultrasound in order to conduct intraoperative prostate brachytherapy in an accurate and consistent manner.

2D Transrectal Ultrasound Guided Permanent Implant Prostate Brachytherapy

Prostate brachytherapy is a form of radiation therapy in which about 80 radioactive seeds (e.g, $^{125}I$) are placed directly into the prostate, either temporarily or permanently. Because the control rates of prostate cancer appear to be dose dependent, it is theorized that the higher doses produced by brachytherapy will yield higher control rates than external-beam radiation without a rise in complications. Recent brachytherapy literature suggests that it has a role in the treatment of early-stage prostate cancer, and also that it may be comparable or even preferable to surgery and external-beam radiation in some patients when evaluated by current therapeutic and economic endpoints.[2]

While removable implant techniques are being developed and used in some institutions, the most common form of brachytherapy involves implanting the sources permanently in the prostate. In either technique, in order to deliver a high conformal dose safely to the prostate, radioactive sources must be positioned accurately within the gland.[2] In the pioneering days of brachytherapy, open laparotomies were performed, and the oncologist inserted seeds directly into the gland either suprapubically or transperneally with manual guidance from the suprapubic or retropubic approach. Without visualizing of the prostate interior from the transperineal approach, accurate positioning of the seeds in three dimensions was impossible Transrectal ultrasound (TRUS), introduced in 1971, allowed direct visualization of the prostate. The introduction in the mid 1980's of higher frequency (5 & 7 MHz) real-time TRUS transducers resulted in higher image resolution and better display of anatomy. Over the past decade the TRUS-guided prostate brachytherapy procedure has increased in popularity. Currently, the most common approach makes use of CT- or ultrasound-based dose pre-implantation plan to determine the total activity and distribution of the radioactive seeds in the prostate. At a later patient visit, the seeds are implanted on an outpatient basis under general or spinal anaesthesia, while the patient is placed in the "same" lithotomy position as the pre-plan. This procedure is now carried out under TRUS guidance, but some institutions use fluoroscopy. After the implantation at a separate patient visit, the actual seed locations are determined with CT or fluoroscopy and a post-implantation plan is generated.

Typically, a biplane TRUS probe is used, which contains a side-firing linear transducer array and an additional curved array positioned near the tip producing an axial view perpendicular to the linear array. The probe is covered with a water-filled condom to allow good contact with the rectal wall. After insertion into the rectum and attachment to brachytherapy assembly, which includes a needle guidance template and a manual stepper, the probe is typically withdrawn in 5 mm steps, while a 2D image is digitized at each step. Since most prostates are about 4 to 5 cm long, this procedure provides 8 to 10 2D transverse images for pre-implant dose planning.

A number of investigators and companies lave developed pre-planning dosimetry software, which accepts 2D transverse ultrasound images.[3] Typically, the margins of the prostate in the 2D images are contoured manually with a mouse and used in the treatment optimization software, which yields source positions for target coverage.

Figure 1:
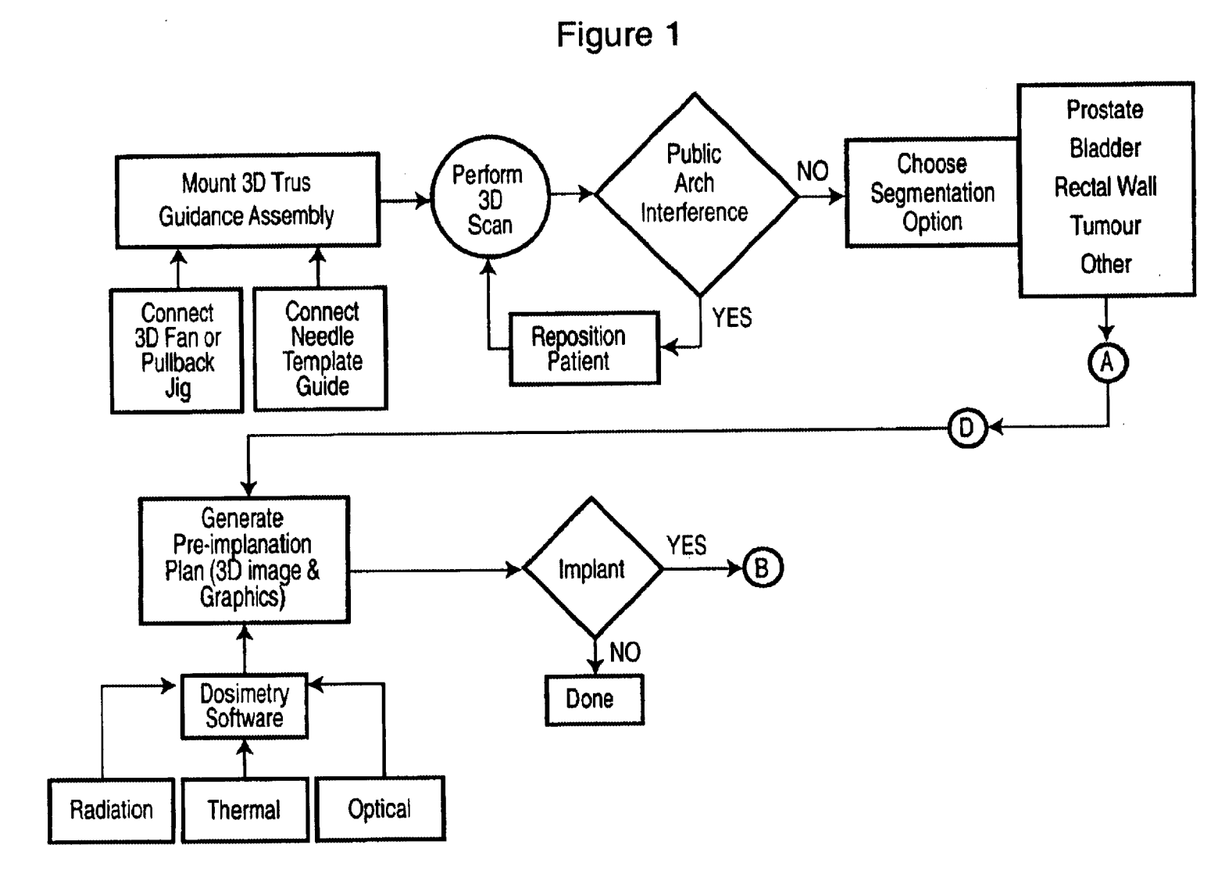
FIG. 1 shows a flow chart of the steps involved and the software modules involved in the pre-implantation step of the present method.
Figure 2:
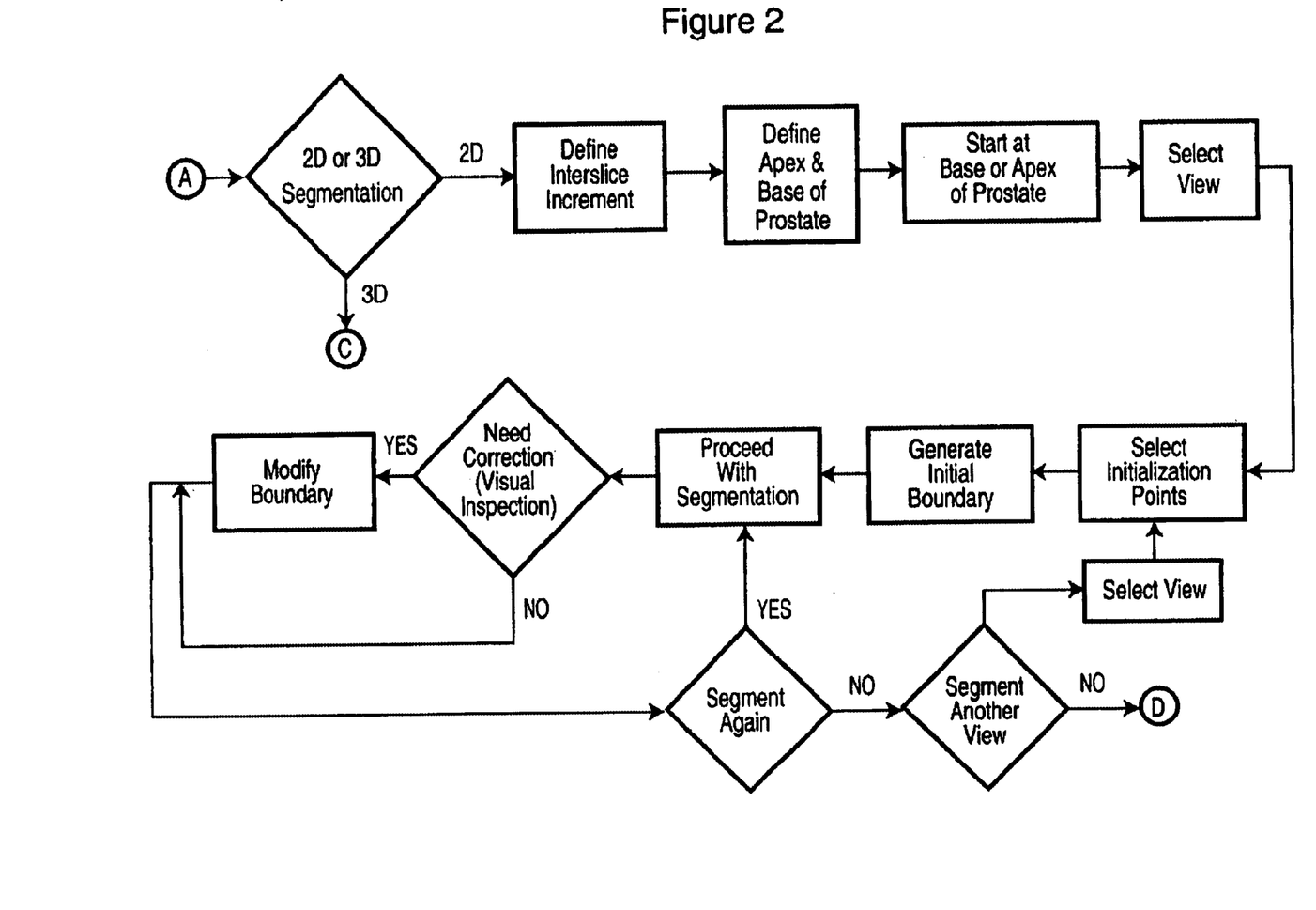
FIG. 2 shows a flow chart of the steps involved and the software modules involved in the segmentation step of the present method.
Figure 3:
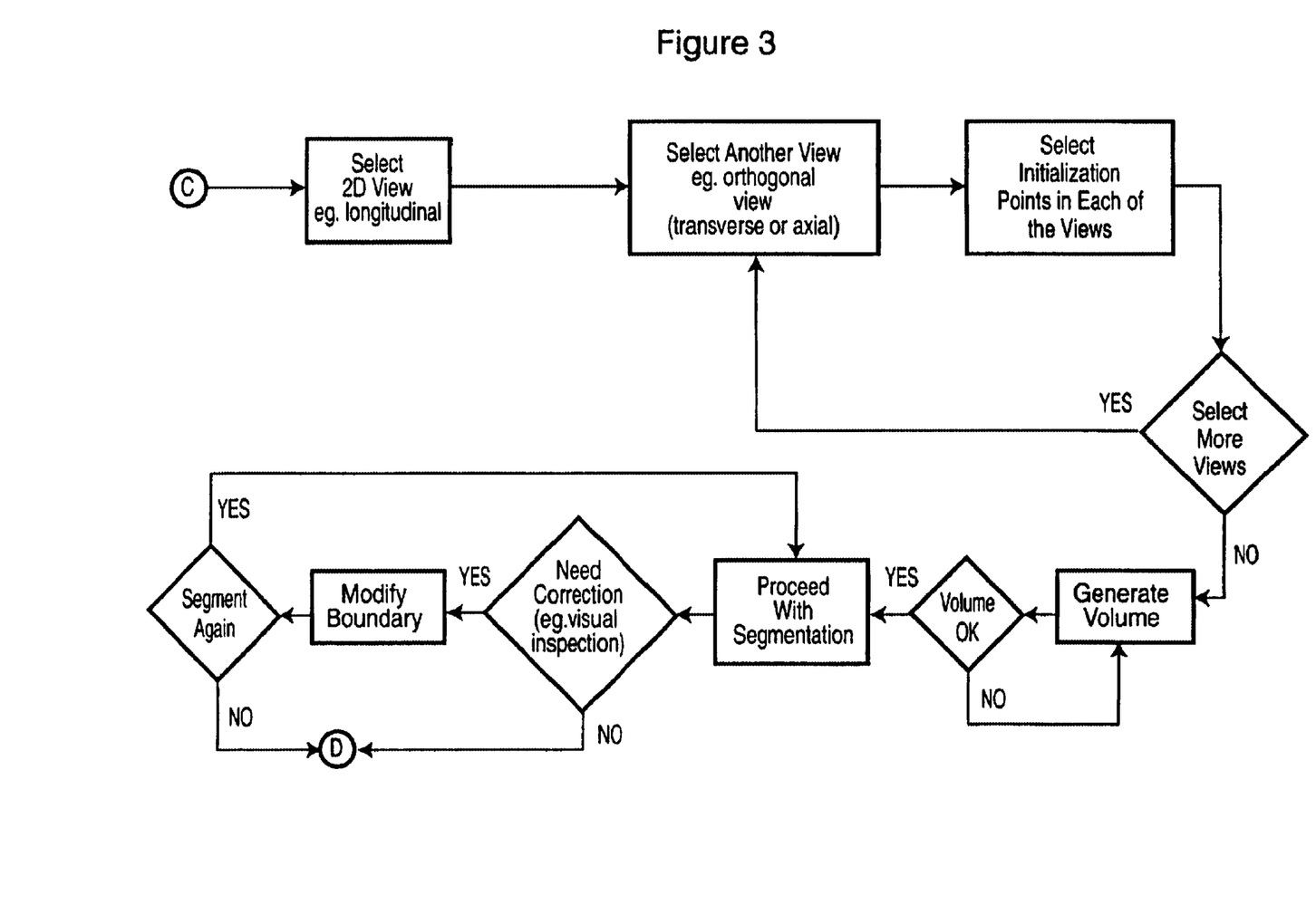
FIG. 3 shows a flow chart of the steps involved and the software modules involved in the segmentation step of the present method.
Figure 4:
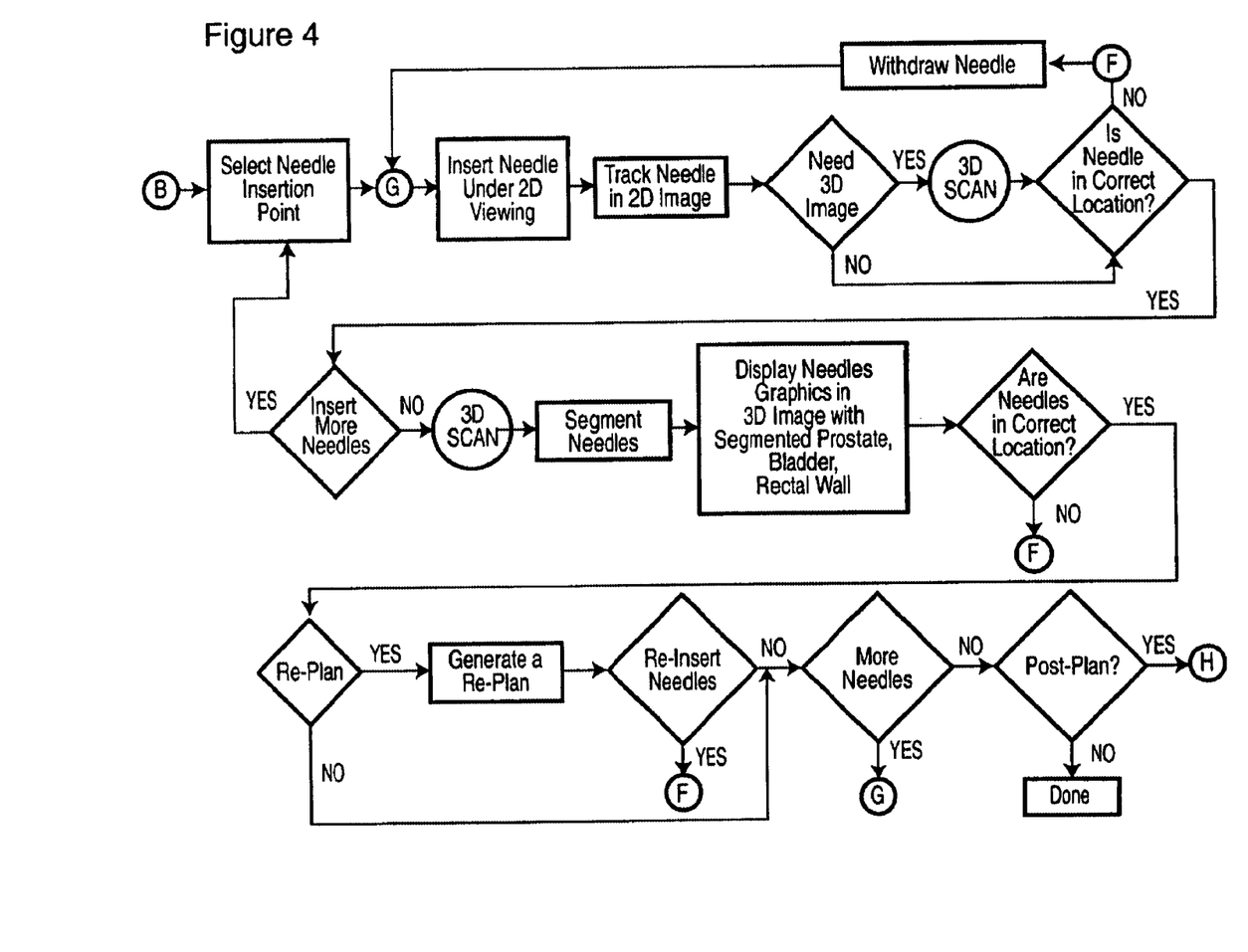
FIG. 4 shows a flow chart of the steps involved and the software modules involved in the implantation step of the present method.
Figure 5:
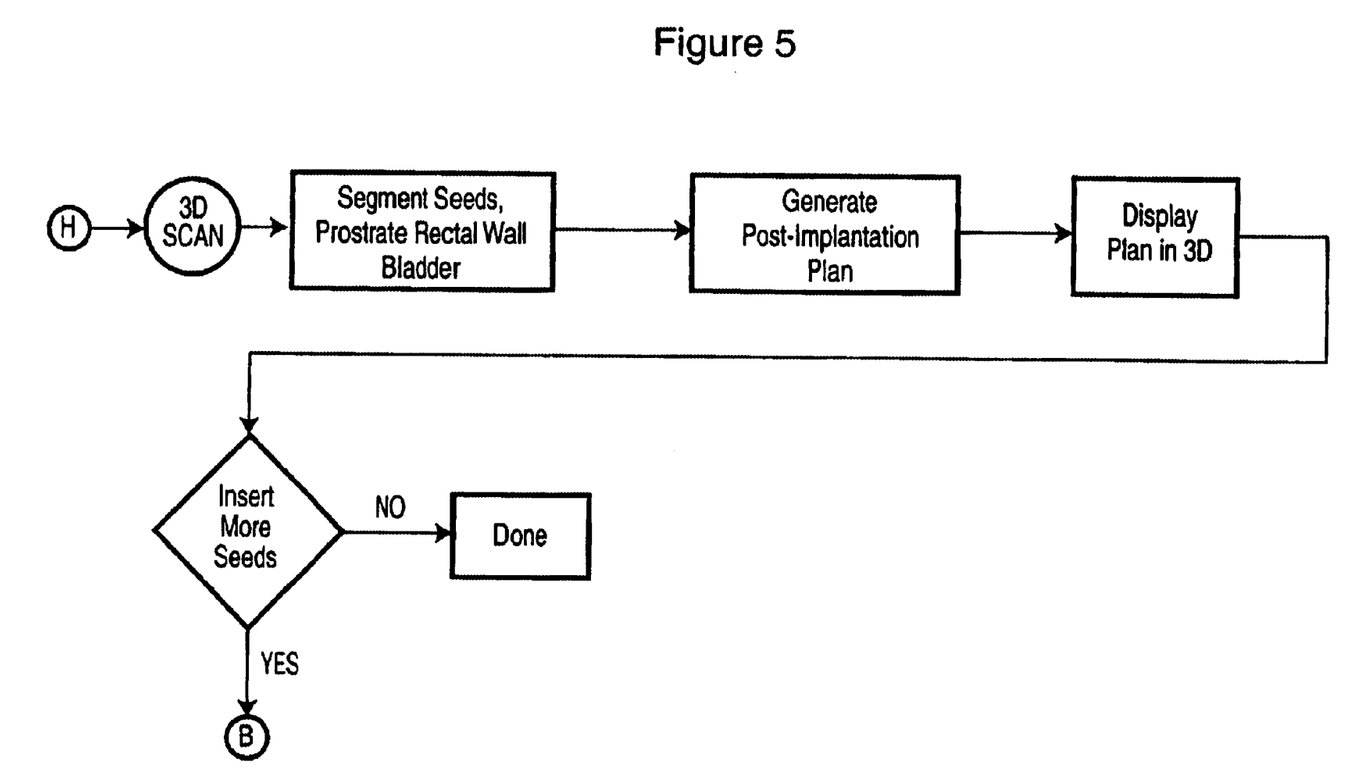
FIG. 5 shows a flow chart of the steps involved and the software modules involved in the post-implantation step of the present method.
Figure 6A:
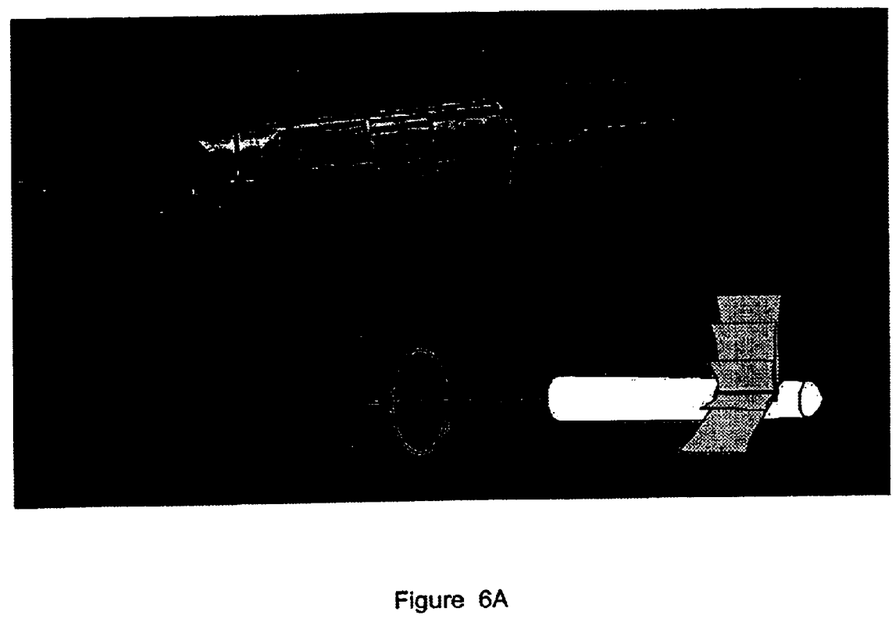
FIG. 6A shows the motorized assembly housing of the side-firing-linear TRUS transducer. When activated, the motor causes the transducer to rotate about its axis.
Figure 6B:
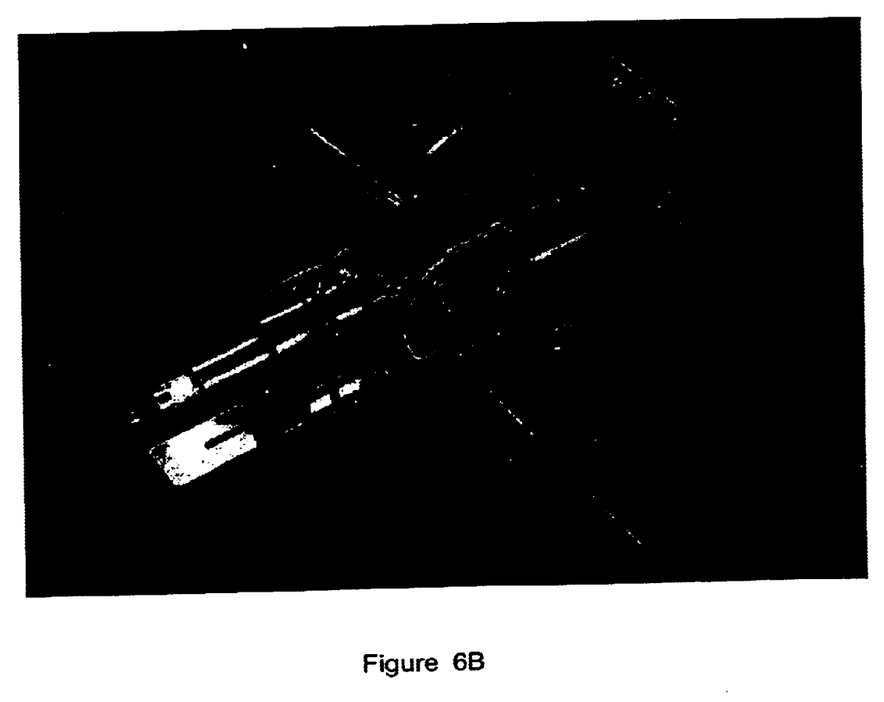
FIG. 6B shows a prostate cancer patient positioned in the lithotomy position for a cryosurgical procedure. The 3D TRUS system is positioned in the rectum with a localizing grid positioned on the patient's penneum.

During the implantation phase, at a subsequent visit, the patient is positioned in a similar orientation to the pre-planning position. Once the TRUS probe is in position, needles are inserted under TRUS guidance. Since the needles are often deflected during insertion, 2D TRUS visualization helps the oncologist to detect the deflection. If the oncologist believes that the deflection is significant, then the needle is reinserted. Because the elevational resolution is poor (beam width of a few mm), use of 2D TRUS is not sensitive to deflection across the beam (FIG. 6). In addition, once several needles have been inserted, visualization is made difficult by the acoustic artifacts produced by the seeds. This can be minimized by inserting the more anterior seeds first, so that the artifacts they produce do not obscure the needles positioned more posteriorly.

Using the 3D TRUS method of the present invention, alleviates some of the technical limitations of 2D TRUS. Moreover, allowing interactive viewing of the prostate in 3D makes it ideal for treatment planning prior to implantation and allows 3D monitoring of seed and needle placement during implantation. This not only enhances placement accuracy, but also allows for needle and seed placement verification. Thus, any detected errors can be compensated for by performing a replan and adjusting subsequent seed locations accordingly.

Limitations of 2D TRUS-guided Brachytherapy Addressed by the Present Invention

Some of the limitations of ultrasound imaging are related to fundamental physical aspects of the interaction of ultrasound with tissues, resolution limitations and the detection of the ultrasound echoes. Progress in overcoming these limitations is being made by the ultrasound machine manufacturers. However, advances in ultrasound imaging afforded by 3D ultrasound will have an equal or greater impact on prostate brachytherapy specifically (and other prostate therapies) with the development of identification, quantification and guidance tools based on 3D TRUS. The present invention addresses the following limitations of 2D ultrasound:

Conventional ultrasound images are 2D, hence, the oncologist must mentally integrate multiple images to develop a 3D impression of the anatomy/pathology during the image guided therapeutic procedure. This practice is time-consuming, inefficient, and requires a highly skilled operator, all of which can potentially lead to incorrect therapeutic decisions Therapeutic decisions require accurate estimation of the tumor and organ volume. The variability in TRUS prostate imaging and volume measurements using a conventional 2D technique is high, because current ultrasound volume measurement techniques assume an idealized elliptical shape and use only simple measures of the width in two view.[5] Although manual contouring of sequential cross-sectional prostate images has reduced this variability, this approach is time-consuming and arduous, making it impractical during an intra-operative procedure. Fast 3D prostate image acquisition with semi-automatic prostate contouring overcomes this problem.

It is difficult to localize the thin 2D ultrasound image plane in the organ, and difficult to reproduce a particular image location at a later time, making 2D TRUS a limited imaging modality for implantation based on a previously obtained set of 2D images, and for follow-up patient studies.

Previous reports have shown that volumes measured with TRUS are substantially lower than those measured with CT and MR and the volumes of the resected glands. Underestimation of the prostate volume can lead to significant underdose of the prostate periphery. This error could be partially due to the assumption that the prostate is elliptic and basing the measurement on diameters from two orthogonal images, or due to the contouring of the prostate using too large a distance between cross-sections.[6] The intraoperative 3D ultrasound imaging method of the present invention incorporates an accurate and precise prostate contouring algorithm which substantially minimizes this problems.

TRUS images deteriorate because of shadowing and multiple echoes as needles and seeds are introduced into the prostate. Thus, identification of individual sources in 2D images is very difficult, requiring the use of CT or fluoroscopy. The use of 3D TRUS images, rather than from just a few (8 to 10) 2D cross-sectional images, provides sufficient information to localize the needles and seeds in the prostate.

Although 2D TRUS-guided prostate planning and implantation is useful in providing a method for treatment of the prostate, and technical strides in prostate brachytherapy have improved the accuracy and consistency of source placement,[4] the 2D TRUS approach still suffers from those disadvantages as described above, which must be overcome before it can be used consistently in a comprehensive intra-operative therapeutic approach. The Applicant has now developed a TRUS-guided intraoperative brachytherapy method using 3D ultrasound which obviates the need for a CT-based preplan. This developed method and system permits planning and implantation at the same session thereby avoiding problems of repositioning, prostate motion, prostate size/contour changes, and image registration between modalities. This also permits post-implant verification, allowing immediate corrections of errors in implantation. The present intra-operative system and method integrates the planning software with semi-automatic prostate contouring, needle and seed detection algorithms and real-time comparisons to the preplan (FIGS. 1–5).

The present invention overcomes the above listed limitations of 2D TRUS by using a 3D TRUS-based system for planning, real-time image-guidance, and post-implant verification of prostate brachytherapy.

In general, the image-guided interventional method of the present invention progresses through three phases: 1) pre-operative planning; 2) implantation; and 3) monitoring. During each phase, various new hardware and software components are used, which are integrated into a useful operating-room system. FIGS. 1–5 show flow charts of the steps in the procedure, as well as details of the procedure and the software modules in each step During the pre-implant planning phase, the optimal distribution of the therapy sources is determined. This requires accurate knowledge of the 3D geometry of the prostate and the sensitive surrounding structures, and an accurate dose planning algorithm. Currently, 2D CT or TRUS images obtained every 5 mm are used with manual prostate contouring as inputs into the dose-planning software. In the present invention, these techniques are replaced with a 3D TRUS technique and semi-automated contouring and integrated with treatment planning software to allow fast on-line planing.

The objective of minimally invasive therapy techniques is to be "conformal", i.e., to give a lethal dose to the entire prostate, while limiting the dose to the surrounding normal structures. Thus, once planning is complete, the implantation phase of the procedure requires exact positioning of needles delivering the individual therapy sources within the prostate. To accomplish this, accurate and precise implantation and verification are crucial. This requires a system that provides accurate and precise geometric information not only at the pre-implant planning stage, but also during the implantation procedure in the operating room. 2D TRUS images do not provide sufficient information to accomplish this accurately. Real-time 2D TRUS is still utilized to visualize the needle, but software tools are added to guide it in the 3D image to the pre-planned location, followed by 3D TRUS to verify the final source locations in 3-dimensions.

Once the therapy has been administered, post-plan verification is important. A CT scan is usually carried out to verify that the seeds are in their planned locations and to generate a post-plan, although corrections are not generally performed. Clearly, fast and accurate tools to perform this task intra-operatively will allow immediate corrections and change the way prostate brachytherapy is performed. The present invention uses software to identify the seeds in the prostate using 3D TRUS, and register each 3D ultrasound image with previous ones (3D TRUS and CT if available), allowing error corrections during the implantation phase (Table 1).

3D TRUS Guidance Assembly

Over the past decade, investigators have refined the conventional TRUS-guided prostate brachytherapy procedure and increased its popularity[7]. The conventional procedure is performed of an outpatient basis under general or spinal anaesthesia, while the patient is placed in the lithotomy position. To reduce the variability and standardize the procedure, a mechanical assembly is used, which houses the TRUS transducer, a stepper unit and a needle template (FIG. 6). The stepper allows the operator to withdraw the transducer in steps (e.g., 5 mm) and collect the sequence of 2D images needed for the pre-plan. This approach allows pre-planning of the procedure, and insertion of the needle according to selected holes in the template (FIGS. 6B and 9) In the present method and system, a rotational 3D scanning assembly is used as described in U.S. Pat. No. 5,454,371 (the contents of which are incorporated herein). The mechanism is composed of a universal mechanical assembly to move the conventional TRUS ultrasound transducer. The mechanical assembly incorporates a motor and a drive, which can cause the transducer to rotate along its long axis at a constant angular velocity.

As the ultrasound transducer is rotated, the sequence of ultrasound images produced by the conventional ultrasound imaging system are digitized and stored in the computer using a conventional video digitizing computer board. The images are reconstructed into a 3D image (FIG. 7) as described by U.S. Pat. Nos. 5,562,095, 5,454,371 and 5,842,473 (the contents of which are incorporated herein).

Figure 8:
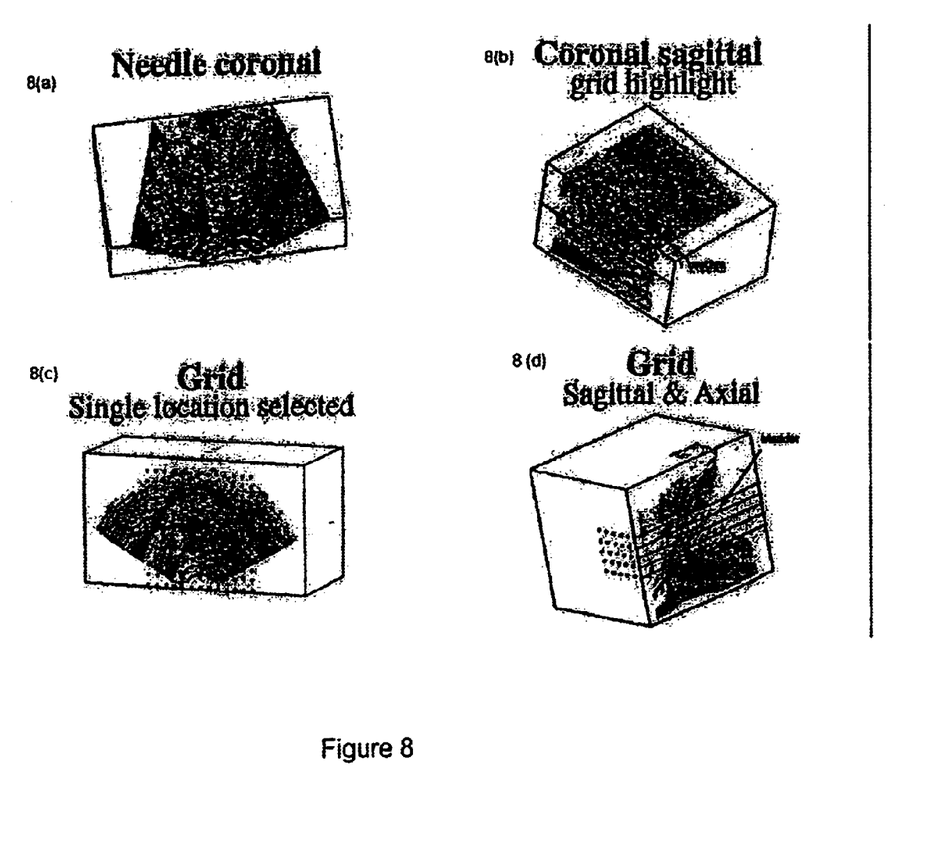
FIG. 8A shows a coronal view of the prostate following insertion of a needle and such view was not available on standard 2D ultrasound. The arrows indicate the prostate edge.
FIG. 8B shows coronal and sagittal views showing a simulated needle trajectory as a superimposed yellow line.
FIG. 8C shows an axial view with simulated localizing grid lines and one selected trajectory.
FIG. 8D shows sagittal and axial views showing the selected needle trajectory.
Figure 9:
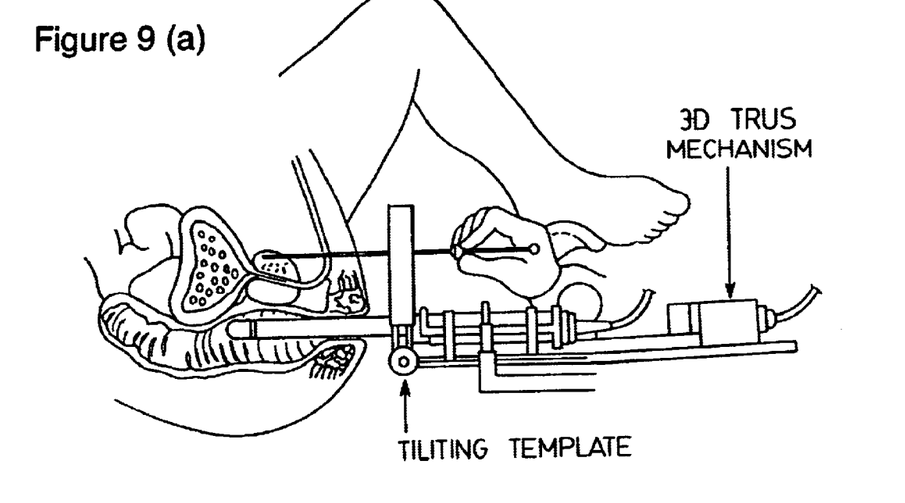
FIG. 9A shows a schematic diagram illustrating the 3D TRUS assembly in position for a 3D scan and a needle being inserted through the tilting needle guidance template.
FIG. 9B shows a schematic diagram showing (a) interference of the pubic arch, and (b) the template being tilted to allow better coverage of the prostate.

When the 3D image is obtained, a series of lines are superimposed onto it, each one corresponding to the projected trajectory of a needle (FIG. 8). The oncologist then views this image before implantation to assess potential pubic arch interference, and after implantation to assess the isodose distributions in 3D.

Prostate Segmentation Algorithm 3D treatment planning requires that the 3D image of the prostate and other anatomical structures (rectal wall, urethra, bladder) be segmented. Currently, prostate images are segmented via manual planimetry. In this approach, the operator manually outlines the prostate and other structures in the 2D images obtained every 5 mm. Since this task is arduous, time-consuming and prone to variability,[0-6] the present approach uses a segmentation algorithm that requires minimal interaction aid processing time.

The objective of The segmentation algorithm is to extract the prostate shape and volume from the image. While segmentation of the prostate is described herein, it is understood by those skilled in the art that the same approach may be applied to the bladder and rectal wall. In situations in which the image contrast is great (e.g., in fluid filled regions in ultrasound images), the segmentation task is relatively easy and many approaches can be used. However, ultrasound images of the prostate are very difficult to segment because the contrast is low, the image suffers from speckle, and parts of the prostate boundary may not be visible due to shadowing and refraction artifacts. In the present invention a semi-automatic approach is used based on active contours that completes the segmentation of the prostate with an error of less than 10%.

Needle Segmentation Algorithm

Figure 11:
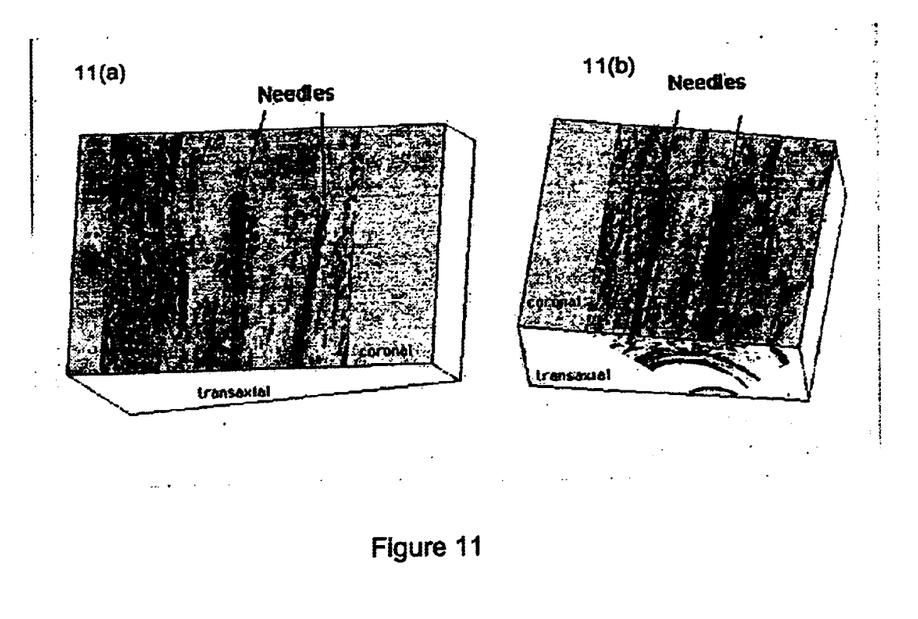
FIG. 11 shows 3D TRUS images obtained during a cryosurgery procedure.

During implantation, needles are inserted approximately perpendicular to the ultrasound beam and withdrawn while dropping radioactive seeds. To ensure that the seeds are dropped at the preplanned positions, the needles must be inserted along the correct trajectory. If significant (>5 mm) errors are detected, the operator must decide whether to withdraw and reinsert the needle. However, using the intra-operative system of the present invention with needle segmentation, then a rapid re-plan (0.5 sec/seed) may be performed by updating the 3D dose distribution based on the real needle trajectory and hypothesized seed locations (e.g., every 5 mm). Although needles are inserted with real-time 2D TRUS guidance, it is the experience from prostate cryosurgery, that because of poor elevational resolution (i.e. thick TRUS beam), lateral deflection is not detected easily. Since the needle is reconstructed from multiple 2D images in 3D TRUS, the trajectory of the needle can be detected in a coronal section (FIG. 11) Clearly, the present efficient method to determine the location of the needle and its true trajectory in the prostate in 3D improves the procedure.

The present method rapidly segments the needles in the 2D and 3D TRUS images for guidance, and in the 3D TRUS images for verification with an error of less than ±1 mm and an angular deflection of less than ±20.

Figure 10:
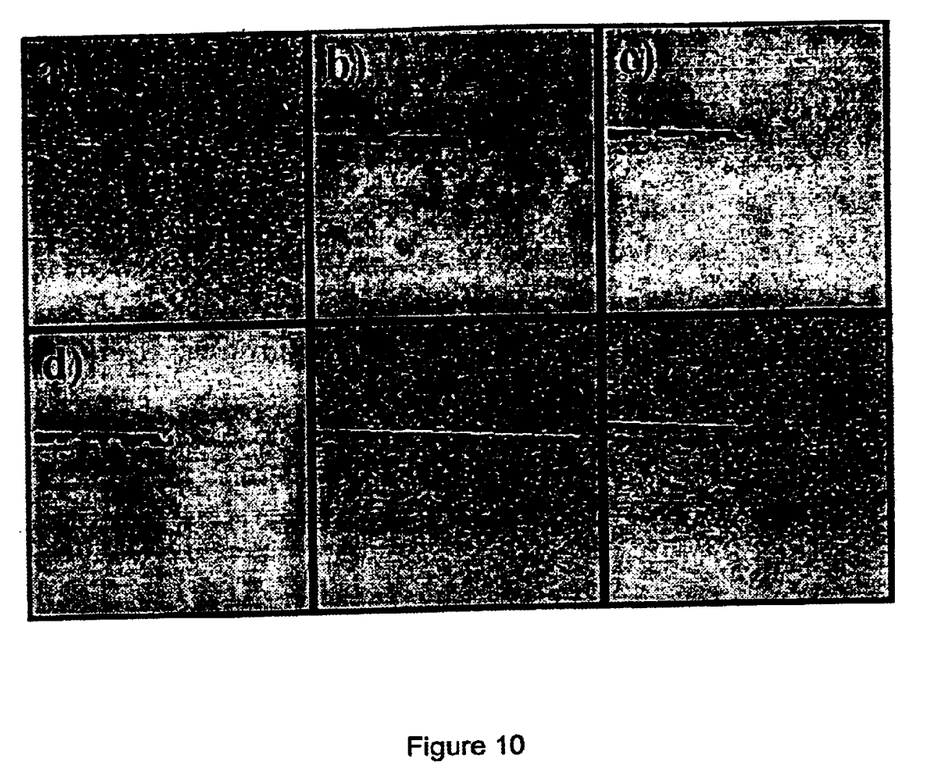
FIG. 10 shows preliminary needle segmentation results. (A) the original ultrasound image showing a needle in the agar phantom. (B) image after convolution with an 11×11 variance kernel. (C) after thresholding. (D) after performing a binary closing operator. (E) after principle component analysis. (F) after detection of needle tip.
Figure 12:
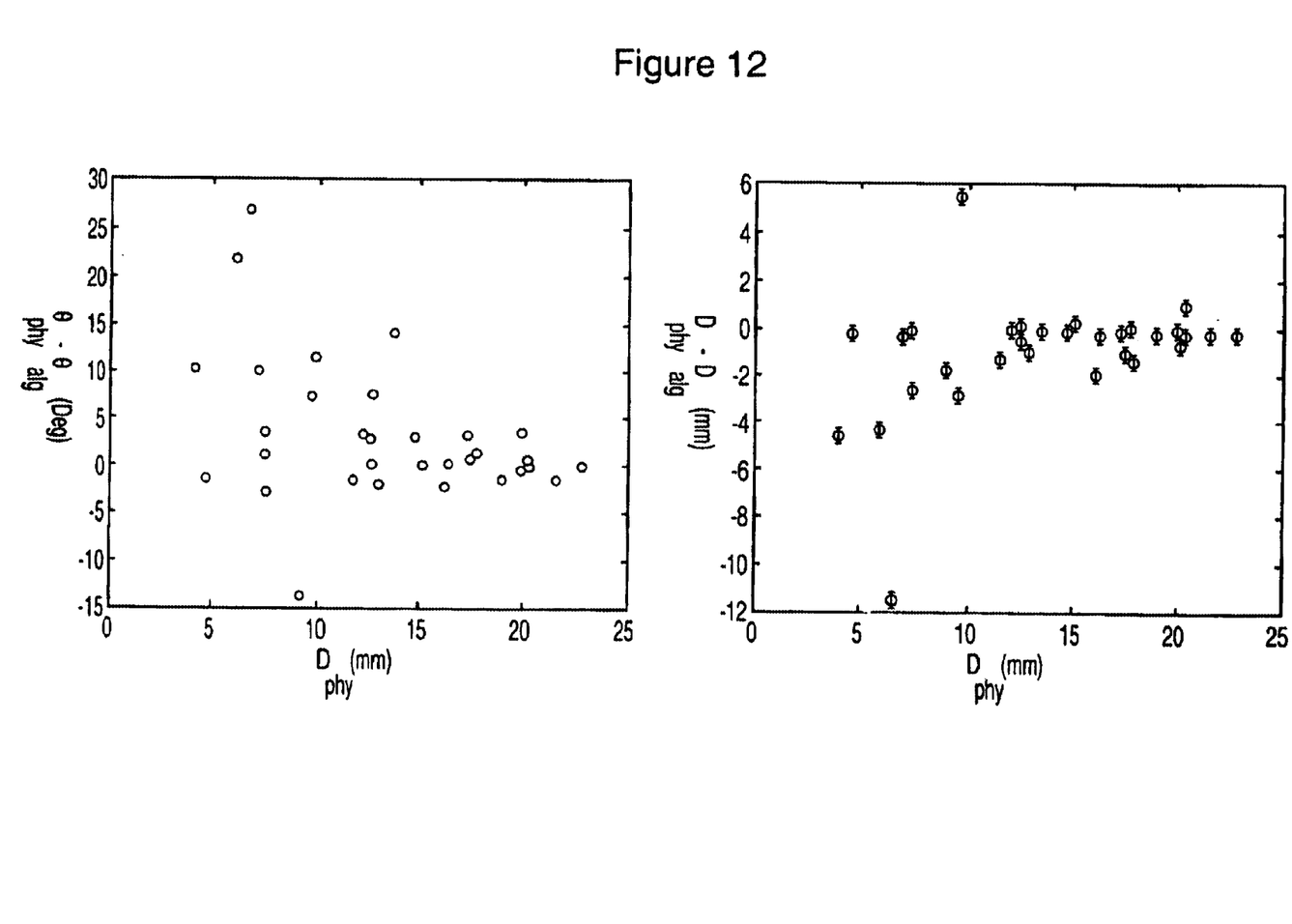
FIG. 12 shows preliminary results of the needle segmentation algorithm. (A) difference in needle trajectory angle between segmentation algorithm and physical measurements, shown versus measured insertion distance $D_{phy}$. Error bars represent observer standard deviations. (B) difference between algorithm and observer segmented tip positions shown versus physical measured tip position. $D_{phy}$. Error bars represent physical measurement uncertainty.

The needle segmentation procedure follows 3 steps. The first step is to enhance the needle contrast by applying a variance filter to the 3D image. The optimum kernel size for this filter is 1 11×11 as shown in FIG. 10. The second step applies a threshold operation and create a binary image. This yields an image composed of clusters of voxels from the needle, and clusters from other specular reflectors. The third step uses principle component analysis to classify each cluster according to its slope and intercept. All clusters from the needle, being collinear, will be similar, so that the others can be eliminated. Results are shown in FIGS. 10 and 12.

Brachytherapy Seed Segmentation Technique

Currently, TRUS is not used for seed location verification because the seeds are too difficult to identify in 2D ultrasound images. Therefore it cannot be used to obtain a post-implant dose distribution. If brachytherapy seeds could be detected consistently and accurately using TRUS, then the post-treatment isodoses could be obtained in the treatment room, thereby removing the necessity of the CT scan and making the brachytherapy procedure more efficient and cost effective.

Prostate brachytherapy is often difficult. Factors such as prostate motion and swelling during implantation, TRUS imaging artifacts, sliding and migration of the seeds in the needle tracks, and needle deflection all contribute to errors between the pre-plan and the actual dose distribution in the prostate. Thus, a verification of the actual locations of the seeds with respect to the prostate margins, rectal wall and bladder is needed imediately after implantation. Although there is no generally accepted verification approach, it is typically done with CT, which shows the sources and prostate margins. Since this is performed after the implantation procedure, it does not permit corrections intra-operatively. This leads to potential inaccuracies since the patient is not necessarily in the identical position as during implantation, and discrepancies have been reported between CT-and TRUS-based prostate volume measurements. Clearly, a technique to identify seed locations intra-operatively in one session is most important, as it allows correction during the procedure, thereby increasing the accuracy and reducing the variability of the procedure. The use of 3D images as in the method of the present invention provides information on the 3D shape of the seeds and gives the information to segment the seeds from the cluttered background.

With 2D TRUS, the accurate delivery of prostate therapy depends on the operator's knowledge of TRUS, his/her skill manipulating the transducer orientation, and facility for mentally reconstructing an accurate 3D impression of the prostate from multiple 2D images. With the present 3D TRUS method and system, multiple (about 100) 2D images are obtained in less than 7 seconds and the 3D image is reconstructed automatically in less than 1 second, making the visualization process faster, more standardized, and more objective, thereby improving the accuracy and reproducibility of the brachytherapy procedure.

The 3D TRUS-based intra-operative procedure of the present invention, with specialized tools for fast and accurate pre-implant planning, implant guidance, implant evaluation, post-implant and long term follow-up, greatly improves current percutaneous prostate brachytherapy by making it more accurate, consistent and cost-effective. Thus approach is less operator-dependent and more reproducible. This represents a major improvement over current practice. The improved prostate visualization afforded by 3D TRUS imaging yields better volume definition, treatment planning, monitoring, follow-up, and overall management of prostate brachytherapy.

It is understood by those skilled in the art that the method and system described herein may also be adapted to other ultrasound guided, minimally invasive prostate therapies, such as cryosurgery, photodynamic therapy, photocoagulation and thermal therapy. Furthermore, the method and system of the present invention may be used for the therapy of other organs, such as the liver, breast and brain.

Variations and modifications of the present invention should be apparent to those of skill in the art without departing from the scope of the present invention as defined by the appended claims.

TABLE 4

Values of the standard error of measurements for determining the coordinates of brachytherapy seeds in 3D ultrasound images of an agar phantom. Also tabulated are the minimum detectible change in the coordinate.

| Coordinate | $SEM_{inter}$ (mm) | $SEM_{intra}$ (mm) | $\Delta_{inter}$ (mm) | $\Delta_{intra}$ (mm) |
|---|---|---|---|---|
| X | 0.30 | 0.28 | 0.82 | 0.78 |
| Y | 0.35 | 0.33 | 0.97 | 0.91 |
| Z | 0.36 | 0.29 | 0.98 | 0.79 |

References

1. Sylvester J, Blasko J C, Grimm P, Radge H: Interstitial implantation techniques in prostate cancer. Journal of Surgical Oncology 66:65–75, 1997.
2. Stokes S H, Real J D, Adams P W, Clements J C, Wuertzer S, Kan W. Transperineal ultrasound-guided radioactive seed implantation for organ-confined carcinoma of the prostate. Int J Radiat Oncol Biol Phys 37:337–34 1, 1997.
3. Nath R, Anderson L L, Luxton G, Weaver K A, Williamson J F, Meigooni A S: Dosimetry of interstitial brachytherapy sources: Recommendations of the AAPM radiation therapy committe task group No.43. Med Phys 22:209–234, 1995.
4. Roberson P L, Narayana V, McShan D L, Winfield R I, McLaughlin P W: Source placement error for permanent implant of the prostate. Med Phys 24:251–7, 1997.
5. Tong S, Cardinal H N, McLoughlin R F, Downey D B, Fenster A: Inra- and Iter-observer Variability and Reliability of Prostate Volume Measurement via 2D and 3D Ultrasound Imaging. Ultrasound in Med & Biol 24:673–681, 1998.
6. Elliot T L, Downey D B, Tong S, Mclean C A, Fenster A: Accuracy of prostate volume measurements in vitro using three-dimensional ultrasound. Acad Radiol 3:401–406, 1996.
7. Edmundson G K, Yan D, Martinez A A: Intraoperative optimization of needle placement and dwell times for conformal prostate brachytherapy. Int J Radiation Oncology Biol Phys 33 No.5:1257–1263, 1995.
8. Tong S, Downey D R, Cards T N, Fenster A: A three-dimensional ultrasound prostate imaging system. Ultrasound Med Biol 22, 735–46, 1996.

We claim:

1. A 3D ultrasound guided intraoperative method for the diagnosis and treatment of diseased tissues, said method comprising the steps of:
    a pre-implant planning phase for producing a 3D tissue image comprising shape and volume of said tissue and surrounding structures and determining optimal distribution of a selected therapy;
    a needle implantation phase for needle segmentation and positioning for delivery of the selected therapy to said tissue;
    a post-plan monitoring phase to verify the therapy implantation and for allowing error correction;
    wherein said needle implantation phase comprises:
        enhancing needle contrast by applying a variance filter to the 3D image;
        applying a threshold operation to create a binary image composed of a cluster of voxels from the needle and other specular reflectors; and
        utilizing principle component analysis to classify each cluster of voxels according to voxel slope and intercept.

2. A 3D ultrasound guided intraopertive method for the diagnosis and treatment of diseased tissues, said method comprising the steps of:
    a pre-implant planning phase for producing a 3D tissue image comprising shape and volume of said tissue and surrounding structures and determining optimal distribution of a selected therapy;
    a needle implantation phase for needle segmentation and positioning for delivery of the selected therapy to said tissue;
    a post-plan monitoring phase to verify the therapy implantation and for allowing error correction;
    wherein said needle implantation phase comprises:
        enhancing needle contrast by applying a variance filter to the 3D image;
        applying a threshold operation to create a binary image composed of a cluster of voxels from the needle and other specular reflectors; and
        utilizing principle component analysis to classify each cluster of voxels according to voxel slope and intercept; and
        wherein said method is used to diagnose and treat prostate cancer.

3. A 3D ultrasound guided intraoperative prostate brachytherapy method for the diagnosis and treatment of prostate cancer, said method comprising:
    a pre-implant planning phase for producing a 3D image of the prostate and surrounding structures and determining optimal distribution of the brachytherapy;
    a needle implantation phase for needle segmentation and positioning for delivery of the brachytherapy to the prostate;
    a post-plan monitoring phase for verifying the needle implantation of the brachytherapy and for allowing error correction during the needle implantation phase;
    wherein said needle segmentation comprises:
        enhancing needle contrast by applying a variance filter to the 3D image;
        applying a threshold operation to create a binary image composed of a cluster of voxels from the needle and other specular reflectors; and
        utilizing principle component analysis to classify each cluster of voxels according to voxel slope and intercept.

4. A 3D Ultrasound guided intraoperative method for the diagnosis and treatment of diseased tissues, said method comprising;
    a pre-implant planning phase for producing a 3D tissue image comprising shape said volume of the tissue and surrounding structures and determining optimal distribution of a selected therapy, said pre-implant planning phase being conducted using 3D ultrasound and a tissue contouring algorithm to extract the 3D tissue image, and wherein a treatment planning algorithm is incorporated in the pre-implant planning phase to allow fast on-line selected therapy planning;
    a needle implantation phase for needle segmentation and positioning for delivery of the selected therapy to the tissue, said needle implantation phase comprising:
        (i) enhancing needle contrast by applying a variance filter to the 3D image;
        (ii) applying a threshold operation to create a binary image composed of a cluster of voxels from the needle and other specular reflectors;
        (iii) utilizing principle component analysis to classify each cluster of voxels according to voxel slope and intercept; and
        (iv) a post-plan monitoring phase to verify the therapy implantation and for allowing error correction.

5. The method of claim 4, wherein said method is used to diagnose and treat diseases of the prostate, liver, breast and brain.

6. A 3D ultrasound guided intraoperative prostate brachytherapy method for the diagnosis and treatment of prostate cancer, said method comprising:
    a pre-implant planning phase for producing a 3D image of the prostate and surrounding structures and determining optimal distribution of the brachytherapy
    a needle implantation phase for needle segmentation and positioning for delivery of the brachytherapy to the prostate, said needle segmentation comprising;
    enhancing needle contrast by applying a variance filter to the 3D image;
    applying a threshold operation to create a binary image composed of a cluster of voxels from the needle and other specular reflectors; and
    utilizing principle component analysis to classify each cluster of voxels according to voxel slope and intercept; and
    a post-plan monitoring phase for verifying the needle implantation of the brachytherapy and for allowing error correction during the needle implantation phase.

* * * * *